United States Statutory Invention Registration [19]

[11] Reg. Number: H327

DiSanzo et al. [43] Published: Sep. 1, 1987

[54] NEMATICIDAL ALKENANILIDES

[75] Inventors: Carmine P. DiSanzo; Clinton J. Peake, both of Medina, N.Y.

[73] Assignee: FMC Corporation, Philadelphia, Pa.

[21] Appl. No.: 549,215

[22] Filed: Nov. 4, 1983

Related U.S. Application Data

[63] Continuation of Ser. No. 349,421, Feb. 16, 1982, abandoned.

[51] Int. Cl.[4] ..... C07C 103/60

[52] U.S. Cl. ..... 564/207; 564/211; 564/212

[58] Field of Search ..... 424/316, 324; 564/207, 564/211, 212

[56] References Cited

U.S. PATENT DOCUMENTS

| | | | |
|---|---|---|---|
| 3,108,038 | 10/1963 | Fielding et al. | 564/207 X |
| 3,278,597 | 10/1966 | Neighbors | 564/207 |
| 3,407,056 | 10/1968 | Schwartz | 564/207 X |
| 3,418,345 | 12/1968 | Baker | 564/207 X |
| 3,657,340 | 4/1972 | Johnson | 564/207 X |
| 3,758,579 | 9/1973 | Martin et al. | 564/207 |
| 4,014,679 | 3/1977 | Perronnet et al. | 564/207 X |

FOREIGN PATENT DOCUMENTS

| | | | |
|---|---|---|---|
| 1219947 | 6/1966 | Fed. Rep. of Germany | 564/207 |
| 245704 | 10/1969 | U.S.S.R. | 564/207 |

OTHER PUBLICATIONS

Stacy et al., "Jour. Amer. Chem. Soc.", vol. 74, pp. 909-911 (1952).

*Primary Examiner*—John F. Terapane
*Assistant Examiner*—Susan Wolffe
*Attorney, Agent, or Firm*—Harrison H. Young, Jr.; H. Robinson Ertelt; Robert L. Andersen

[57] ABSTRACT

A method is described for the control of nematodes in agricultural crops which comprises applying to the situs of infestation a nematicidal composition containing as active ingredient a compound of the formula

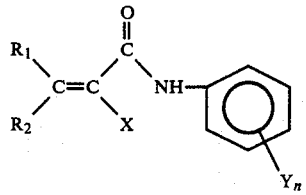

wherein $R_1$ and $R_2$ are hydrogen, lower alkyl, or halogen, X is hydrogen or halogen, n is 1 or 2, Y is hydrogen, lower alkyl, halogen, trifluoromethyl, lower alkoxy, lower alkylthio, and nitro when n is 1, and halogen when n is 2, with the proviso that at least 1 of $R_1$, $R_2$, and X must be halogen. Preparation of active ingredient compounds is described, and nematicidal utility of compositions is exemplified.

5 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

NEMATICIDAL ALKENANILIDES

This application is a continuation, of application Ser. No. 349,421 now abandoned, filed Feb. 16, 1982.

This invention relates to a composition and a method for controlling nematodes. More particularly, the invention relates to the use of derivatives of α-haloacrylic acid as a nematicide for agricultural crops.

Nematicidally active α,β-dihalopropananilides were disclosed in U.S. Pat. No. 2,987,800 (1960). Nematicidally active alkenanilides with no substitution of halogen in the alkenyl group were disclosed in U.S. Pat. No. 3,108,038 (1963). A 1966 Japanese publication (C.A. 65, 13598e) discloses preparation of α-chloroacryl- and α-chlorocrotonylanilides for antifungal testing (in which the compounds were not strongly active). A 1968 Russian publication (C.A. 69, 106164w) reports preparation of α-chloroacrylanilides as potential plant growth regulators; the same investigator disclosed preparation of α-bromo-, β-bromo-, and α,β-dibromoacrylanilides in a 1972 Russian publication (C.A. 78, 42990p). Two patents, U.S. Pat. Nos. 3,758,579 (1973) and 3,881,909 (1975) disclose α-bromoacrylanilides having utility as plant regulators, specifically in regulating abscission of citrus fruit and olives. U.S. Pat. No. 3,840,599 (1974) discloses chloroalkenyl- and chloroalkanylanilides with antifungal utility. No references have been found in which α-haloalkenanilides are disclosed to have utility as nematicides.

The present invention comprises a method for controlling nematodes in agricultural crops by applying to the situs of infestation a nematicidally effective amount of a compound of the formula

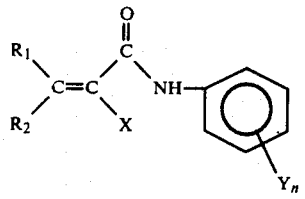

wherein $R_1$ is hydrogen, lower alkyl, and halogen;

$R_2$ is hydrogen, lower alkyl, and halogen;

X is hydrogen and halogen;

with the proviso that at least one of $R_1$, $R_2$, and X must be halogen;

Y is hydrogen, lower alkyl, halogen, trifluoromethyl, lower alkoxy, lower alkylthio, and nitro when n is 1; and Y is halogen when n is 2.

Preferred compounds for use in the method of the invention are those compounds in which $R_1$ and $R_2$ are hydrogen and X is chlorine or bromine; or in which $R_1$ is hydrogen, $R_2$ is methyl, and X is bromine.

In preferred compounds especially preferred for use in the method of the invention, n is 1 and Y is 4-chloro, 4-bromo-, 4-methyl, 4-methoxy, 4-methylthio, 4-nitro, 2-fluoro, 3-fluoro, or 4-fluoro.

When $R_2$ is alkyl (methyl, for example) and $R_1$ is hydrogen and X is halogen, the alkyl and halogen are cis relative to the double bond and the compound is designated [Z]. When $R_2$ is hydrogen, and $R_1$ is alkyl, the alkyl is trans to halogen at X, and the compound is designated [E]. The [Z] isomer is preferred to the corresponding [E] isomer (or to a mixture of [Z] and [E] isomers). When $R_1$ or $R_2$ is halogen, the position of this halogen cis or trans relative to halogen at X dictates the

[Z] or [E] designation, rather than the position of an alkyl group. When X is hydrogen and $R_1$ or $R_2$ is halogen, the position of the halogen cis or trans relative to the carbonyl group dictates the [Z] or [E] designation. The preference for the [Z] isomer over the [E] isomer is not so striking in these latter two situations.

The nematicidal compositions of this invention are those in which the active ingredient is present in admixture with an agriculturally acceptable carrier, diluent, or extender.

The nematicides of this invention, like most agricultural chemicals, are generally not applied full strength, but are formulated with agriculturally acceptable carriers normally employed for facilitating the dispersion of active ingredients, various additives, and optionally with other active ingredients, recognizing the accepted fact that the formulation and mode of application of a toxicant may affect the activity of the material. The present compounds may be applied, for example, to the soil in which nematode control is desired as granules or powders or liquids, the choice of application varying, of course, with the nematode species and environmental factors present at the particular locus of infestation. Thus, the compounds may be formulated as granules of various sizes, as dusts, as wettable powders, as emulsifiable concentrates, as solutions, as dispersions, as controlled release compositions, and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of from about 0.5% up to about 99.5% by weight of the formulation. Substantially inactive ingredients such as adjuvants and carriers may comprise from about 99.5% by weight to as low as about 0.5% by weight of the formulation. Surface active agents, if employed in the formulation, may be present at various concentrations, suitably in the range of 1 to 30% by weight. Provided below is a general description of exemplary types of formulations which may be employed for dispersion of the nematicides of the present invention.

Dusts are admixtures of the active ingredient with finely divided solid carriers and/or diluents such as talc, natural clays, kieselguhr, pyrophyllite, chalk, diatomaceous earths, calcium phosphates, calcium and magnesium carbonates, sulfur, lime, flours, and other organic and inorganic solid carriers. These finely divided formulations generally have an average particle size of less than about 45 μm (No. 325, U.S.A. Standard Sieve Series). In most cases, the active ingredient will be present in dust formulations at a concentration in the range of 1 to 15%, and occasionally from 1% to about 30%, the balance of the composition typically being agriculturally acceptable carrier or diluent.

Wettable powders, also useful formulations for these nematicides, are in the form of finely divided particles which disperse readily in water or other liquid vehicles. The wettable powder is ultimately applied to the soil or plant as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp < 100° C.) are suitably formulated in the concentration range of 5 to 50% by weight, usually from 10 to 30%; high melting solids (mp > 100° C.) are formulated in the range of 5 to 95% by weight, usually 50 to 85%. An agriculturally acceptable carrier or diluent, frequently including a small amount of a surfactant to facilitate wetting dispersion and suspension, accounts for the balance of the formulation.

Granules are admixtures of the active ingredients with solids of particle sizes generally in the range of 4.75 mm to 150 μm (No. 4 to No. 100, U.S.A. Standard Sieve Series). Granular formulations may employ hard core materials such as sands and other silicates, mineral carbonates, sulfates or phosphates and the like, or porous cores such as attapulgite clays, fuller's earth, kieselguhr, chalk, diatomaceous earths, ground corn cobs, wood dusts and the like. Impregnating or binding agents such as aliphatic and aromatic petroleum solvents, alcohols, ethers, ketones, esters, vegetable oils, polyvinyl acetates, polyvinyl alcohols, dextrins, sugars and the like are commonly used to aid in coating or impregnating the solid carriers with the active ingredient. Emulsifying agents, wetting agents, dispersing agents, and other additives known in the art may also be added.

A typical granular formulation may suitably contain from about 1% to about 50% by weight active ingredient and 99% to 50% by weight of inert materials.

Microencapsulated or other controlled release formulations may also be used with nematicides of this invention for control of nematodes.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application of the nematicide, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5 to 5% being surfactant and liquid carrier.

Flowables are similar to EC's except that the active ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in nematicidal formulations include, but are not limited to, the alkyl and alkylaryl sulfonates and sulfates and their sodium salts; alkylamide sulfonates, including fatty methyl taurides; alkylaryl polyether alcohols, sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the nematicidal composition.

Other useful formulations include simple solutions of the active ingredient in a relatively non-volatile solvent such as corn oil, kerosene, propylene glycol, or other organic solvents. This type of formulation is particularly useful for ultra low volume application.

The concentration of the nematicide in use dilution is normally in the range of about 2% to about 0.1%. Many variations of spraying, dusting, soil-incorporated, and controlled or slow release compositions in the art may be used by substituting or adding a compound of this invention into compositions known or apparent to the art.

Nematicidal compositions may be formulated and applied with other suitable active ingredients, including other nematicides, insecticides, acaricides, fungicides, plant regulators, herbicides, fertilizers, or with synergists.

In applying the foregoing chemicals, whether alone or with other agricultural chemicals, an effective nematicidal amount must be applied. While the application rate will vary widely depending on the choice of compound, the formulation and mode of application, the plant species being protected and the planting density, a suitable use rate may be in the range of 0.5 to 25 kg/hectare, preferably 1 to about 20 kg/hectare. Trees and vines for example may require at least 5 kg/hectare whereas annuals such as corn may require considerably lower rates of application, for example 1 to 5 kg/hectare.

Preparation of the nematicidal compounds and of intermediates from which they are prepared is described in the following examples. In the descriptions which follow, all temperatures are in degrees Celsius, and reduced pressures are shown in Pascals (Pa); pressures not so designated are pressures normally attainable using a water aspirator.

Example 1

2-Bromo-N-phenyl-2-propenamide

Step A Synthesis of 2-bromo-2-propenoic acid as an intermediate

A stirred solution of 84.9 grams (0.366 mole) of 2,3-dibromopropionic acid in an appropriate amount of water was cooled to 0°±5°. To this was added dropwise 184 ml of aqueous 2N sodium hydroxide at such a rate that the reaction mixture temperature did not exceed 10°. An additional 184 ml of aqueous 2N sodium hydroxide was added dropwise. Upon completion of addition, the reaction mixture was allowed to warm to ambient temperature where it was stirred for one hour. The clear reaction mixture was acidified with 47 ml of concentrated hydrochloric acid and extracted with three portions of 400 ml each of diethyl ether. The combined extracts were dried with magnesium sulfate and filtered. The filtrate was concentrated under reduced pressure to give a solid residue. The solid was recrystallized from hexane to give 41.6 grams of 2-bromo-2-propenoic acid; mp 69.5°–71.5°.

Step B Synthesis of 2-bromopropenoyl chloride as an intermediate

A stirred solution prepared by adding 20.6 grams (0.173 mole) of thionyl chloride to 16.4 grams (0.108 mole) of 2-bromo-2-propenoic acid (Step A product) was heated at 70°±5° for 18 hours. The reaction mixture was allowed to cool to ambient temperature, and was then distilled under reduced pressure to give 9.5 grams of 2-bromopropenoyl chloride as an oil; bp 71°-73°.

Step C Synthesis of 2-bromo-N-phenyl-2-propenamide

A vigorously stirred solution of 4.5 grams (0.027 mole) of 2-bromopropenoyl chloride (Step B product) in 150 ml of dried methylene chloride was cooled to 5°±5°. To this was added dropwise 4.0 grams (0.027 mole) of N,N-diethylaniline at such a rate that the reaction mixture temperature did not exceed 10°. Upon completion of addition, 2.5 grams (0.027 mole) of aniline was added dropwise while continuing to maintain the reaction mixture temperature below 10°. The reaction mixture was allowed to warm to ambient temperature where it was stirred for two hours. After dilution with 100 ml of aqueous 1N hydrochloric acid, the reaction mixture was poured into a separatory funnel. The organic layer was separated and extracted with 50 ml of aqueous 1N hydrochloric acid, then with 100 ml of an aqueous solution saturated with sodium bicarbonate. The organic layer was dried with magnesium sulfate. The mixture was filtered and the filtrate concentrated under reduced pressure to a residual solid. The solid was dissolved in methylene chloride and decolorized with silica gel. The mixture was filtered and the filtrate concentrated under reduced pressure to a residual solid. The solid was recrystallized from hexane to give 4.0 grams of 2-bromo-N-phenyl-2-propenamide; mp 90.5°-92.5°.

The nmr and the ir spectra were consistent with the assigned structure.

Analysis calc's for $C_9H_8BrNO$: C 47.82; H 3.56; N 6.19; Found: C 47.60; H 3.57; N 6.08.

EXAMPLE 2

2-Chloro-N-(4-chlorophenyl)-2-propenamide

Step A Synthesis of 2,3-dichloro-N-(4-chlorophenyl)-propanamide as an intermediate To a stirred solution of 12.8 grams (0.10 mole) of 4-chloroaniline in 85 ml of chloroform was added 8 ml of pyridine. The mixture was cooled to 10° and 16.1 grams (0.10 mole) of 2,3-dichloropropionyl chloride was added dropwise at such a rate that the reaction mixture temperature did not exceed 35°. Upon completion of addition, the reaction mixture was stirred at ambient temperature for 16 hours. The reaction mixture was concentrated under reduced pressure to a solid residue. The solid was slurried with water and collected by filtration. The dried solid was recrystallized from methylcyclohexane-ethyl acetate using silica gel as a decolorant to give 19.7 grams of 2,3-dichloro-N-(4-chlorophenyl)propanamide; mp 127.5°-129°.

The nmr and the ir spectra were consistent with the assigned structure.

Analysis calc'd for $C_9H_8Cl_3NO$: C 42.81; H 3.19; N 5.55; Found: C 42.79; H 3.28; N 5.57.

Step B Synthesis of 2-chloro-N-(4-chlorophenyl)-2-propenamide

To a stirred solution of 17.0 grams (0.067 mole) of 2,3-dichloro-N-(4-chlorophenyl)propanamide (Step A product) in 300 ml of toluene was added dropwise 11.3 grams (0.074 mole) of 1,8-diazabicyclo[5.4.0]-undec-7-ene in 100 ml of toluene. Upon completion of addition, the reaction mixture was stirred at ambient temperature for 60 hours. The reaction mixture was diluted with distilled water and transferred to a separatory funnel. The organic layer was separated and washed twice with water and twice with an aqueous solution saturated with sodium chloride. The organic layer was dried with magnesium sulfate and filtered. The filtrate was concentrated under reduced pressure to a residual solid. The solid was recrystallized from methylcyclohexane using silica gel as a decolorant to give 7.4 grams of 2-chloro-N-(4-chlorophenyl)-2-propenamide; mp 105°-106.5°.

The nmr and the ir spectra were consistent with the assigned structure.

Analysis calc'd for $C_9H_7Cl_2NO$: C 50.03; H 3.27; N 6.48; Found: C 50.16; H 3.38; N 6.55.

EXAMPLE 3

[Z]-2-Bromo-N-(3-fluorophenyl)-2-butenamide

Step A Synthesis of 2,3-dibromobutanoic acid as an intermediate

A stirred solution of 86.1 grams (1.0 mole) of crotonic acid in 500 ml of carbon tetrachloride was cooled to 2°. The reaction vessel containing the solution was covered with aluminum foil to exclude light. To this solution was added dropwise 167.8 grams (1.05 moles) of bromine. The complete addition required one hour during which time the reaction mixture temperature rose to 8°. The reaction vessel was packed in wet ice and the reaction mixture stirred for 16 hours. During this time the reaction mixture had warmed to ambient temperature. The solvent was removed under reduced pressure to give 236 grams of 2,3-dibromobutanoic acid; mp 83°-86°.

The nmr and the ir spectra were consistent with the assigned structure.

Step B Synthesis of [Z]-2-bromo-2-butenoic acid as an intermediate

Pyridine, 23.7 grams (0.30 mole), was added to 24.6 grams (0.10 mole) of 2,3-dibromobutanoic acid (Step A product). The resultant solution was stirred as it was heated for two hours at 75°-80°. The reaction mixture was cooled to 10° and acidified to pH 1 with 48 ml of 18.5% hydrochloric acid. The resultant solid was collected by filtration and washed with water. The dried solid had a mp of 105°-107°. The filtrate was extracted with three portions of 50 ml each of diethyl ether. The combined extracts were dried with magnesium sulfate and filtered. The filtrate was concentrated under reduced pressure to give 6.4 grams of solid with a mp of 102°-104° when dried. The two solids were combined to give 9.3 grams of [Z]-2-bromo-2-butenoic acid; mp 104°-106°.

The nmr spectrum was consistent with the assigned structure.

Step C Synthesis of [Z]-2-bromo-2-butenoyl chloride as an intermediate

Thionyl chloride, 404.7 grams (3.402 moles) was added dropwise to 374.2 grams (2.268 moles) of stirred [Z]-2-bromo-2-butenoic acid (Step B product). The resultant solution was stirred at ambient temperature for 16 hours, then heated at reflux for one hour. The reaction mixture was distilled under water aspirator vacuum to give 379.1 grams of [Z]-2-bromo-2-butenoyl chloride; bp 61°-65° C./$1.07\times10^3$ Pa.

Step D Synthesis of [Z]-2-bromo-N-(3-fluorophenyl)-2-butenamide

To a stirred solution of 4.2 grams (0.038 mole) of 3-fluoroaniline in 35 ml of chloroform was added 3.1 ml of pyridine. The reaction mixture was cooled to 0° and 7.0 grams (0.038 mole) of [Z]-2-bromo-2-butenoyl chloride (Step C product) was added dropwise at such a rate that the reaction mixture temperature did not exceed 10°. Upon completion of addition, the reaction mixture was stirred at 0° for one hour, then was allowed to warm to ambient temperature where it was stirred for 16 hours. The reaction mixture was washed with 10 ml of water, two portions of 10 ml each of aqueous 0.1N hydrochloric acid, 10 ml of water, and finally 10 ml of an aqueous solution saturated with sodium chloride. The organic layer was dried with sodium sulfate and filtered. The filtrate was concentrated under reduced pressure to a residual oil. The oil was crystallized from hexane using silica gel as a decolorant to give 6.7 grams of [Z]-2-bromo-N-(3-fluorophenyl)-2-butenamide; mp 44°-45.5°.

The nmr and the ir spectra were consistent with the assigned structure.

Analysis calc'd for $C_{10}H_9BrFNO$: C 46.54; H 3.51; N 5.43; Found: C 46.56; H 3.67; N 5.25.

EXAMPLE 4

[Z]-2,3-Dibromo-N-(4-chlorophenyl)propenamide

Step A Synthesis of [E,Z]-2,3-dibromopropenoic acid as an intermediate

The reaction vessel containing a stirred solution of 50.0 grams (0.694 mole) of propynoic acid in 1470 ml of water was covered to exclude as much light as possible. To this solution was added dropwise 110.9 grams (0.694 mole) of bromine at such a rate that the reaction mixture temperature did not exceed 30°. Upon completion of addition the reaction mixture was stirred for two hours, then was extracted with five portions of 100 ml each of diethyl ether. The combined extracts were dried with magnesium sulfate and filtered. The filtrate was concentrated under reduced pressure to a clear residual oil. The oil was slurried with 700 ml of boiling hexane and the hot hexane was decanted from some insoluble material and reserved (Solution A-1). The insoluble residue was slurried with 300 ml of boiling hexane and the hot hexane was again decanted from insoluble material and reserved (Solution A-2). The remaining insoluble material was dissolved in a hot mixture of 50 ml hexane-30 ml ethyl acetate; after slurrying with silica gel to remove impurities the mixture was filtered.

The approximately 700 ml of Solution A-1 was cooled to give an off-white solid which was collected by filtration; mp 65°-67.5°. Nuclear magnetic resonance (nmr) spectroscopy indicated the solid to be [E]-2,3-dibromopropenoic acid. The yield was 24.8 grams.

The approximately 300 ml of Solution A-1 and the filtrate from Solution A-2 were combined and concentrated under reduced pressure to give 70 grams of a yellow oil. The oil was dissolved in 130 ml of hexane and the solution cooled in a freezer. A solid precipitate was collected by filtration. NMR spectroscopy indicated the solid to be [E,Z]-2,3-dibromopropenoic acid. The [E,Z] acid was recrystallized from methylcyclohexane using silica gel as a decolorant. The yield was 17.0 grams; mp 49°-51°. The mother liquor from this recrystallization was combined with the filtered 50 ml hexane-30 ml ethyl acetate solution above. This combination was concentrated under reduced pressure to give 49.5 grams of [Z]-2,3-dibromopropenoic acid as an oil. The oil was combined with the 17.0 grams of [E,Z] acid to give 66.5 grams of [E,Z]-2,3-dibromopropenoic acid.

Analysis calc'd for $C_3H_2Br_2O_2$: C 15.68; H 0.88; Found: C 15.86; H 1.15.

Step B Synthesis of [E,Z]-2,3-dibromopropenoyl chloride as an intermediate

This compound was prepared in the manner of Example 1, Step B, using 66.4 grams of [E,Z]-2,3-dibromopropenoic acid and 51.6 grams (0.434 mole) of thionyl chloride. The product was combined with 1.8 grams from another run of this reaction and distilled under reduced pressure. The distillation isolated 20.1 grams of pure [Z]-2,3-dibromopropenoyl chloride; bp 73°-78°/$2.00\times10^3$ Pa.

The ir spectrum was consistent with the assigned structure.

Step C Synthesis of [Z]-2,3-dibromo-N-(4-chlorophenyl)propenamide

This compound was prepared in the manner of Example 3, Step D, using 4.2 grams (0.032 mole) of 4-chloroaniline, 7.5 grams (0.030 mole) of [Z]-2,3-dibromopropenoyl chloride, and 2.7 ml of pyridine in 30 ml of chloroform. The yield of [Z]-2,3-dibromo-N-(4-chlorophenyl)propenamide was 4.1 grams; mp 99.5°-100.5°.

The nmr and the ir spectra were consistent with the assigned structure.

Analysis calc'd for $C_9H_6Br_2ClNO$: C 31.85; H 1.78; N 4.13 Found: C 32.80; H 2.00; N 4.29

EXAMPLE 5

[E]-3-Chloro-N-(4-methylphenyl)-2-butenamide

Step A Synthesis of ethyl [E,Z]-3-chloro-2-butenoate as an intermediate

In a reaction vessel flushed with argon gas was placed 437.4 grams (3.36 moles) of ethyl acetoacetate in 500 ml of methylene chloride. The stirred solution was cooled to 0° C. and 700 grams (3.36 moles) of phosphorous pentachloride was added in portions at a rate such that the reaction mixture temperature did not exceed 5°. Upon completion of addition, the reaction mixture was stirred at 0°-5° for 16 hours. Five-hundred ml of water was added dropwise, and the layers in the resultant two-phase system were separated. The water layer was made alkaline with solid sodium bicarbonate and extracted with several 100-ml portions of methylene chloride. The organic layer from the reaction mixture was washed with water until all the solid material in it dissolved. The washed organic layer and the methylene chloride washings of the water layer were combined and dried with sodium sulfate. The mixture was filtered and the filtrate concentrated under reduced pressure to a residual oil. The oil was first distilled under reduced pressure using a Vigreux column. Fractions boiling at 52°-65°/$0.40-1.07\times10^3$ Pa were combined and subjected to a second distillation under reduced pressure using a spinning band distilling system. Fractions boiling at 66°-70°/$0.40-1.07\times10^3$ Pa from the first distillation and fractions boiling at 66.5°-82°/$1.20\times10^3$ Pa from the second distillation were subjected to a third distillation under reduced pressure using a spinning band distilling system. The fraction, bp 46°/$1.33\times10^3$ Pa from the second distillation was combined with the fractions, bp 42°-45°/$1.20\times10^3$ Pa from the third distillation to give 38.4 grams of ethyl [E]-3-chloro-2-butenoate.

Analysis calc'd for $C_6H_9ClO_2$: C 48.50; H 6.11; Found C 48.57; H 6.00.

The fraction, bp 75°-85°C/$0.40-1.07\times10^3$ Pa from the first distillation was recrystallized from cold hexane to give a solid; mp 58°-60°. Nmr spectroscopy indicated the solid to be [E]-3-chloro-2-butenoic acid. A second impure crop was also collected. The mother liquor from this recrystallization was combined with the pot residue from the third distillation to give 114.5 grams of ethyl [Z]-3-chloro-2-butenoate.

Step B Synthesis of [E]-3-chloro-2-butenoic acid as an intermediate

A stirred mixture of 38.4 grams (0.258 mole) of ethyl [E]-3-chloro-2-butenoate in 96 ml of concentrated hydrochloric acid and 96 ml of water was heated under reflux for 18 hours. The reaction mixture was cooled to ambient temperature and extracted with methylene chloride. The combined extracts were concentrated under reduced pressure to a solid residue. Ihe solid was recrystallized from hexane using silica gel as a decolorant to give 10.5 grams of [E]-3-chloro-2-butenoic acid; mp 59°-60°.

Step C Synthesis of [E]-3-chloro-2-butenoyl chloride as an intermediate

This compound was prepared in the manner of Example 1, Step B, using 66.0 grams (0.548 mole) of [E]-3-chloro-2-butenoic acid and 97.7 grams (0.821 mole) of thionyl chloride. The yield of [E]-3-chloro-2-butenoyl chloride was 55.6 grams; bp 54°-59°/4.00-4.27$\times 10^3$ Pa.

Step D Synthesis of [E]-3-chloro-N-(4-methylphenyl)-2-butenamide

This compound was prepared in the manner of Example 3, Step D, using 10.7 grams (0.10 mole) of 4-methylaniline, 13.9 grams (0.10 mole) of [E]-3-chloro-2-butenoyl chloride and 8 ml of pyridine in 85 ml of chloroform. The yield of [E]-3-chloro-N-(4-methylphenyl)-2-butenamide was 17.3 grams; mp 108°-109°.

The nmr and the ir spectra were consistent with the assigned structure.

Analysis calc'd for $C_{11}H_{12}ClNO$: C 63.01; H 5.77; N 6.68; Found: C 63.02; H 5.62; N 6.55.

The method of Example 1 was employed to prepare the following compound; the nmr and ir spectra were consistent with the assigned structure:

Example 6. 2-Bromo-N-(4-methoxyphenyl)-2-propenamide; mp 86.5°-87.5°; analysis calc'd: C 46.89, H 3.93, N 5.46; found: C 46.82, H 3.99, N 5.58.

The method of Example 2 was employed to prepare the following compounds; the nmr and ir spectra were consistent with the assigned structure:

Example 7. 2-Chloro-N-phenyl-2-propenamide; mp 56°-57°; analysis calc'd: C 58.86, H 4.39, N 7.63; found: C 59.70, H 4.67, N 7.69.

Example 8. 2-Chloro-N-(4-methylphenyl)-2-propenamide, mp 60°-61.5°; analysis calc'd: C 61.39, H 5.15, N 7.16; found: C 61.43, H 5.18, N 7.23.

Example 9. 2-Chloro-N-(4-methoxyphenyl)-2-propenamide; mp 78°-79°; analysis calc'd: C 56.75, H 4.76, N 6.62; found: C 56.49, H 4.78, N 6.76.

Example 10. 2-Chloro-N-(2-chlorophenyl)-2-propenamide; mp 41°-42°; analysis calc'd: C 50.03, H 3.27, N 6.48; found: C 50.09, H 3.37, N 6.75.

Example 11. 2-Chloro-N-(3-chlorophenyl)-2-propenamide; mp 85°-86°; analysis calc'd: C 50.03, H 3.27, N 6.48; found: C 49.80, H 3.29, N 6.67.

Example 12. N-(4.Bromophenyl)-2-chloro-2-propenamide; mp 113.5°-115.5°; analysis calc'd: C 41.49, H 2.71, N 5.38; found: C 41.71, H 2.87, N 5.66.

Example 13. 2-Chloro-N-(4-iodophenyl)-2-propenamide; mp 110°-111°; analysis calc'd: C 35.15, H 2.29; N 4.55; found: C 35.09, H 2.50, N 4.50.

Example 14. 2-Bromo-N-(4-chlorophenyl)-2-propenamide; mp 89.5°-90°; analysis calc'd: C 41.49, H 2.70, N 5.37; found: C 41.26, H 2.86, N 5.25.

Example 15. 2-Bromo-N-(4-methylphenyl)-2-propenamide; mp 72°-73°; analysis calc'd: C 50.02, H 4.19, N 5.83; found: C 50.18, H 4.20, N 6.11.

Example 16. 2-Bromo-N-(3,4-dichlorophenyl)-2-propenamide; mp 81.5°-82.5°; analysis calc'd: C 36.64, H 2.05, N 4.74; found: C 36.62, H 2.05, N 4.56.

Example 17. 2-Bromo-N-(3-methoxyphenyl)-2-propenamide; mp 76°-77.5°; analysis calc'd: C 46.90, H 3.94, N 5.47; found: C 47.12, H 3.91, N 5.49.

Example 18. 2-Bromo-N-phenyl-2-butenamide; mp 91.5°-92.5°; analysis calc'd: C 50.02, H 4.20, N 5.83; found: C 50.30, H 4.37, N 5.74.

Example 19. [Z]-2-Bromo-N-phenyl-2-butenamide; mp 34°-36°; analysis is that shown for Example 18.

Example 20. 2-Bromo-N-(4-methylphenyl)-2-butenamide; mp 51.5°-64°; analysis calc'd: C 51.99, H 4.76, N 5.51; found: C 51.86, H 4.68, N 5.24.

Example 21. [Z]-2-Bromo-N-(4-methylphenyl)-2-butenamide; mp 74°-76°; analysis is that shown for Example 20.

Example 22. 2 Bromo-N-(3,4-dichlorophenyl)-2-butenamide; mp 56°-60°; analysis calc'd: C 38.87, H 2.61, N 4.53; found: C 38.99, H 2.72, N 4.43.

Example 23. 2-Bromo-N-(4-chlorophenyl)-2-butenamide; mp 108°-112°; analysis calc'd: C 43.75, H 3.30, N 5.10; found: C 43.49, H 3.35, N 5.06.

Example 24. 2-Bromo-N-(4-methoxyphenyl)-2-butenamide; mp 79°-80°; analysis calc'd: C 48.91, H 4.48, N 5.19; found: C 48.83, H 4.52, N 5.14.

The method of Example 3 was employed to prepare the following compounds; the nmr and ir spectra were consistent with the assigned structures:

Example 25. [Z]-2-Chloro-N-(4-chlorophenyl)-2-butenamide; mp 89.5°-90.5°; analysis calc'd C 52.20, H 3.94, N 6.09; found: C 52.07, H 3.90, N 5.95.

Example 26. [Z]-2-Chloro-N-(4-methylphenyl)-2-butenamide; mp 82°-83.5°; analysis calc'd: C 63.01, H 5.77, N 6.68; found: C 62.93, H 5.60, N 6.64.

Example 27. [Z]-2-Chloro-N-(4-methoxyphenyl)-2-butenamide; mp 75°-77°; analysis calc'd: C 58.54, H 5.36, N 6.21; found: C 57.95, H 5.18, N 6.16.

Example 28. [Z]-2-Bromo-N-(4-chlorophenyl)-2-butenamide; mp 75°-76°; analysis calc'd: C 43.75, H 3.30, N 5.10; found: C 43.89, H 3.43, N 4.99.

Example 29. [Z]-2-Bromo-N-(4-methoxyphenyl)-2-butenamide; mp 87°-88°; analysis calc'd: C 48.91, H 4.48, N 5.19; found: C 48.56, H 4.43, N 5.07.

Example 30. [Z]-2-Bromo-N-(3,4-dichlorophenyl)-2-butenamide; mp 93°-94°; analysis calc'd: C 38.87, H 2.61, N 4.53; found: C 38.97, H 2.82, N 4.51.

Example 31. [Z]-2-Bromo-N-(4-bromophenyl)-2-butenamide; mp 94.5°-96°; analysis calc'd: C 37.65, H 2.84, N 4.39; found: C 37.95, H 2.89, N 4.35.

Example 32. [Z]-2-Bromo-N-(4-iodophenyl)-2-butenamide; mp 114°-115°; analysis calc'd: C 32.82, H 2.48, N 3.83; found: C 33.11, H 2.39, N 3.80.

Example 33. [Z]-2-Bromo-(4-nitrophenyl)-2-butenamide; mp 130°-131°; analysis calc'd: C 42.13, H 3.18, N 9.83; found: C 42.93, H 3.32, N 9.72.

Example 34. [Z]-2-Bromo-N-(4-ethylphenyl)-2-butenamide; mp 67°-68°; analysis calc'd: C 53.75, H 5.26, N 6.22; found: C 53.97, H 5.28, N 5.07.

Example 35. [Z]-2-Bromo-N-[4-(methylthio)phenyl]-2-butenamide; mp 98°-99°; analysis calc'd: C 46.16, H 4.23, N 4.89; found: C 46.50, H 4.40, N 4.51.

Example 36. [Z]-2-Bromo-N-[4-(trifluoromethyl)-phenyl]-2-butenamide; mp 93°-94.5°; analysis calc'd: C 42.88, H 2.94, N 4.55; found: C 43.14, H 3.18, N 4.29.

Example 37. [Z]-2-Bromo-N-(2-fluorophenyl)-2-butenamide; bp 80°-94°/3.33 Pa; analysis calc'd: C 46.S54, H 3.51, N 5.43; found: C 45.96, H 3.59, N 5.35.

Example 38. [Z]-2-Bromo-N-(4-fluorophenyl)-2-butenamide; mp 58°-59°; analysis calc'd: C 46.54, H 3.51, N 5.43; found: C 46.77, H 3.81, N 5.12.

Example 39. [Z]-2-Bromo-N-phenyl-2-pentenamide; mp 52°-53°; analysis calc'd; C 51.99, H 4.76, N 5.51; found: C 52.06, H 4.69, N 5.42.

Example 40. [Z]-2-Bromo-N-(4-chlorophenyl)-2-pentenamide; mp 76.5°-78°; analysis calc'd: C 45.78, H 3.84, N 4.85; found: C 45.97, H 3.94, N 4.80.

Example 41. [Z]-2-Bromo-N-(4-methylphenyl)-2-pentenamide; mp 40°-41°; analysis calc'd: C 53.74, H 5.26, N 5.22; found: C 53.65, H 5.44, N 5.12.

Example 42. [Z]-2-Bromo-N-(4-methoxyphenyl)-2-pentenamide; mp 52°-53°; analysis calc'd: C 50.72, H 4.97, N 4.93; found: C 50.75, H 5.10, N 4.77.

Example 43. [Z]-2-Bromo-N-(3,4-dichlorophenyl)-2-pentenamide; mp 77.5°-79°; analysis calc'd: C 40.90, H 3.72, N 4.34; found: C 41.02, H 3.32, N 4.20.

The method of Example 4 was employed to prepare the following compounds; the nmr and ir spectra were consistent with the assigned structures:

Example 44. [Z]-2,3-Dibromo-N-(4-methylphenyl)-propenamide; mp 87°-89°; analysis calc'd: C 37.65, H 2.84, N 4.39; found: C 38.65, H 3.15, N 4.55.

Example 45 [Z]-2,3-Dibromo-N-(4-methoxyphenyl)-propenamide; mp 123.5°-124°; analysis calc'd: C 35.85, H 2.71, N 4.18; found: C 35.84, H 2.94, N 3.92.

The method of Example 5 was employed to prepare the following compounds; the nmr and ir spectra were consistent with the assigned structures:

Example 46. [E]-3-Chloro-N-phenyl-2-butenamide; mp 104°-105°; analysis calc'd: C 61.39, H 5.15, N 7.16; found: C 61.20, H 4.98, N 7.21.

Example 47. [E]-3-Chloro-N-(4-chlorophenyl)-2-butenamide; mp 134°-136°; analysis calc'd: C 52.20, H 3.94, N 6.09; found: C 52.41, H 3.85, N 5.99.

Example 48 [E]-3-Chloro-N-(4-methoxyphenyl)-2-butenamide; mp 90°-91.5°; analysis calc'd: C 58.54, H 5.36, N 6.21; found: C 58.56, H 5.27, N 5.96.

Example 49. [E]-3-Chloro-N-(3,4-dichlorophenyl)-2-butenamide; mp 125°-126°; analysis calc'd: C 45.40, H 3.05, N 5.29; found: C 45.15, H 3.04, N 5.05.

Example 50. [Z]-3-Chloro-N-phenyl-2-butenamide; mp 121°-121.5°; analysis calc'd: C 61.39, H 5.15, N 7.16; found: C 61.60, H 5.19, N 7.05.

Example 51 [Z]-3-Chloro-N-(4-methoxyphenyl)-2-butenamide; mp 105°-106.5°; analysis calc'd: C 58.54, H 5.36, N 6.21; found: C 58.66, H 5.10, N 6.10.

Example 52. [Z]-3-Chloro-N-(4-chlorophenyl)-2-butenamide; mp 130°-131°; analysis calc'd: C 52.20, H 3.94, N 6.09; found: C 52.29, H 4.02, N 5.96.

Example 53. [Z]-3-Chloro-N-(4-methylphenyl)-2-butenamide; mp 107.5°-108.5°; analysis calc'd: C 63.01, H 5.77, N 6.68; found: C 63.12, H 5.55, N 6.73.

Biological Testing

The compounds of Examples 1°-53 were formulated and tested for nematicidal activity as formulated materials. The formulation used was a standard 5 weight percent dust formulation made up as follows:

| | |
|---|---|
| Active ingredient (100% active basis) | 5 parts |
| Base | 95 parts |
| 96%-attapulgite clay | |
| 2%-highly purified sodium lignosulfonate (100%) | |
| 2%-powdered sodium alkylnaphthalenesulfonate (75%); | |

the mixture was ground to a fine powder.

The formulations described above were tested for activity against root-knot nematode (*Meloidogyne incognita*) as follows:

*Nematode Culture*—Tomato seedlings with two large true leaves were transplanted into six inch clay pots containing steam-sterilized sandy soil. One week after transplanting, galled roots of nematode-infected tomato plants, with fully developed egg masses, were placed in three holes in the soil around the seedling roots. Holes were then closed with soil. The plants were allowed to grow until fully developed egg masses were formed (6 to 7 weeks after inoculation).

*Inoculum Preparation*—Infected tomato roots, containing egg masses, were cleaned under running tap water, cut into short pieces and comminuted with water in an electrical blender for 30 seconds. The shredded roots were poured onto layers of washed sand in a wooden flat. The flat was covered with plastic sheeting and kept at greenhouse temperatures for 3 to 7 days to allow about 50% of the larvae to hatch.

*Preparation of Root-Knot Nematode Infested Soil*—Samples of the infested soil prepared as described above were processed for nematodes by using the Caveness and Jensen centrifugal-sugar flotation extraction technique [Caveness, F. E. and Jensen, H. J., "Modification of the Centrifugal Flotation Technique for the Isolation and Concentration of Nematodes and their Eggs from Soil and Plant Tissue", Proc. Helm. Soc., Washington, 22, 87-89 (1955).]

Fine wire cloth screen (No. 500, U.S.A. Standard Sieve Series) was used to collect the nematodes and eggs, and their number was estimated under a stereomicroscope. Enough sand containing eggs and larvae was mixed with additional steam-sterilized sandy soil so that there were 600 to 800 root-knot nematode larvae and eggs per pot of soil (three inch diameter each, containing approximately 300 g soil). Depending on the total amount of nematode infested soil needed, mixing was accomplished by use of a cement mixer for 5 minutes or a V-shaped rotary mixer for 60 seconds.

Soil so infested was used for soil incorporated nematicidal studies within 2 days of preparation. The formulated compounds to be tested for nematicidal activity were incorporated in the potting soil infested with root-knot nematodes to give soil treatment at rates of 25 ppm, 10 ppm, and 5 ppm (weight chemical/volume soil). Young tomato plants were planted in this soil in three-inch pots. Untreated check plants were treated in the same manner as those treated with the active ingredient. The formulation base, without active ingredient, was added to the soil for untreated plants and separate untreated plants were used to detect the effects, if any, of chemicals in the formulation base. Each test series also included a formulation of carbofuran, a known nematicide, as a standard for comparison.

At the end of two weeks the roots of all plants were examined and rated in comparison to untreated checks, using the following system:

Knot Index

4—No control—amount of swellings equivalent to that developed on the roots of the untreated check plants.

3—Amount of swellings 25% less than that developed on the roots of the untreated check plants.

2—Amount of swellings 50% less than that developed on the roots of the untreated check plants.

1—Amount of swellings 75% less than that developed on the roots of the untreated check plants.

0—No swellings—complete control.

When the control observed is between 1 and 0 the Knot Index is subdivided to indicate how close the control is to 75% or to 100%. For this subdivision numbers between 0 and 1 are used as follows:

| | |
|---|---|
| 0.8 | 80% control |
| 0.5 | 90% control |
| 0.4–0.1 | 95–99% control |

The knot index for the untreated check was 4.0. Results for the compositions of the invention are recorded in Table I.

Evaluation of compositions of the invention against stunt nematode (*Tylenchorhynchus claytoni*) was carried out by incorporating the formulated active ingredient in soil in which a corn seedling was then planted, and two days thereafter inoculating the soil with stunt nematode in mixed stages of growth, from larvae to adults. The soil was processed for nematode counting approximately five weeks after treatment. Untreated check plants showed no nematode control. Results with formulations of the invention are recorded in Table II as "Percent Control" relative to nematode control in the untreated check pot. The compositions tested showed control ranging from 75% to 100%.

Compositions were also evaluated against lesion nematode (*Pratylenchus penetrans*), following a similar procedure in which pea seedlings were planted instead of corn seedlings, and nematodes were extracted from the root systems, instead of from the soil. Untreated plants showed no nematode control. Results with formulations of the invention are recorded in Table III. Activity was generally lower than that observed against stunt nematodes. Twenty compositions of 31 tested showed some degree of control of lesion nematodes; five exhibited control above 70%.

Various modifications may be made in the formulation and application of the novel compositions of this invention without departing from the inventive concept herein, as defined in the claims below.

TABLE I

Activity Against Root Knot Nematodes of Alkenanilides
Soil Incorporated as 5% Dust at 25, 10, 5 ppm

| Compound of Example | Knot Index[1], Average[2] 25 ppm | 10 ppm | 5 ppm |
|---|---|---|---|
| 1 | 0 | .15 | .75 |
| 2 | 0 | 0 | 0 |
| 3 | 0 | .33 | .58 |
| 4 | 0 | 3.30 | 4.00 |
| 5 | .57 | 1.70 | 3.00 |
| 6 | 0 | 0 | 1.70 |
| 7 | 0 | 0 | 1.60 |
| 8 | 0 | .12 | .65 |
| 9 | 0 | 0 | .50 |
| 10 | 1.00 | 4.00 | 4.00 |
| 11 | 0 | 3.30 | 4.00 |
| 12 | 0 | 0.82 | 4.00 |
| 13 | 0.12 | 4.00 | 4.00 |
| 14 | 0 | .03 | 0 |
| 15 | 0 | 0 | .13 |
| 16 | 0 | 1.67 | 3.25 |
| 17 | 0 | 1.13 | 1.75 |
| 18 | — | 1.50 | 4.00 |
| 19 | 0 | 0 | 1.70 |
| 20 | — | 3.00 | 4.00 |
| 21 | 0 | 0 | .90 |
| 22 | 0.90 | 3.30 | 4.00 |
| 23 | 0 | 1.20 | 4.00 |
| 24 | 1.00 | 4.00 | 4.00 |
| 25 | 0 | 0 | 1.80 |
| 26 | .37 | 2.30 | 4.00 |
| 27 | 3.30 | 4.00 | 4.00 |
| 28 | 0 | 0 | .17 |
| 29 | 0 | 0 | .95 |
| 30 | 0 | .50 | 1.20 |
| 31 | 0 | 0 | .57 |
| 32 | 0 | .87 | 3.00 |
| 33 | 0 | 0 | .37 |
| 34 | 0 | .37 | 3.30 |
| 35 | 0 | 0 | .62 |
| 36 | 0 | .90 | 2.30 |
| 37 | 0 | 0 | .33 |
| 38 | 0 | .37 | 1.00 |
| 39 | .58 | 3.00 | 4.00 |
| 40 | 0 | .70 | 4.00 |
| 41 | .12 | 4.00 | 4.00 |
| 42 | 3.70 | 4.00 | 4.00 |
| 43 | 4.00 | 4.00 | 4.00 |
| 44 | 0 | .85 | 4.00 |
| 45 | .82 | 4.00 | 4.00 |
| 46 | 1.80 | 3.50 | 4.00 |
| 47 | 1.40 | 1.10 | 4.00 |
| 48 | 1.50 | 2.00 | 4.00 |
| 49 | 4.00 | 4.00 | 4.00 |
| 50 | 3.70 | 4.00 | 4.00 |
| 51 | .87 | 3.70 | 4.00 |
| 52 | 0 | 2.20 | 4.00 |
| 53 | 1.80 | 4.00 | 4.00 |

Explanation of Knot Index in text.
Average of four replicates. Untreated check plants showed no nematode control (Knot Index = 4.0).

TABLE II

Activity Against Stunt Nematodes of Alkenanilides
Soil Incorporated as 5% Dust at 20, 15, 10 ppm

| Compound of Example | Percent Control[1,2] 20 ppm | 15 ppm | 10 ppm |
|---|---|---|---|
| 1 | — | 94 | — |
| 2 | 100 | — | — |
| 6 | 99 | — | — |
| 7 | 99 | — | — |
| 8 | 100 | — | — |
| 9 | 100 | — | — |
| 12 | — | — | 80 |
| 18 | 85 | — | — |
| 19 | 75 | — | — |
| 20 | 84 | — | — |
| 21 | 81 | — | — |

TABLE II-continued

Activity Against Stunt Nematodes of Alkenanilides
Soil Incorporated as 5% Dust at 20, 15, 10 ppm

| Compound of Example | Percent Control[1,2] | | |
|---|---|---|---|
| | 20 ppm | 15 ppm | 10 ppm |
| 22 | 89 | — | — |
| 23 | 95 | — | — |
| 24 | 75 | — | — |
| 25 | 83 | — | — |
| 28 | 95 | — | 79 |
| 29 | 97 | — | 80 |
| 30 | 89 | — | 84 |
| 47 | 77 | — | — |

[1]Average of 3-4 replicates. Untreated check showed no control.
[2]Percent control is $$\frac{\left(\text{Average Nematode Count in Check}\right) - \left(\text{Average Nematode Count in Treated Soil}\right)}{\left(\text{Average Nematode Count in Check}\right)} \times 100$$

TABLE III

Activity Against Lesion Nematodes of Alkenanilides
Soil Incorporated as 5% Dust at 25, 20, 15, 10 ppm

| Compound of Example | Percent Control[1,2] | | | |
|---|---|---|---|---|
| | 25 ppm | 20 ppm | 15 ppm | 10 ppm |
| 1 | — | 91 | — | — |
| 2 | 59 | — | — | 0 |
| 3 | — | 47 | — | — |
| 6 | — | 91 | — | 0 |
| 7 | — | — | 28 | 0 |
| 8 | — | — | 65 | 0 |
| 9 | — | — | 13 | 30 |
| 12 | — | 95 | 80 | — |
| 15 | 72 | — | — | 22 |
| 18 | — | — | — | 0 |
| 19 | — | 12 | — | 11 |
| 20 | — | — | — | 3 |
| 21 | — | 42 | — | 0 |
| 22 | — | — | — | 0 |
| 23 | — | — | — | 0 |
| 24 | — | — | — | 0 |
| 25 | — | 14 | — | — |
| 28 | 32 | — | — | 0 |
| 29 | — | 0 | — | 0 |
| 30 | — | 0 | — | 0 |
| 31 | — | 0 | — | — |
| 32 | — | 21 | — | — |
| 33 | — | 0 | — | — |
| 34 | — | 0 | — | — |

TABLE III-continued

Activity Against Lesion Nematodes of Alkenanilides
Soil Incorporated as 5% Dust at 25, 20, 15, 10 ppm

| Compound of Example | Percent Control[1,2] | | | |
|---|---|---|---|---|
| | 25 ppm | 20 ppm | 15 ppm | 10 ppm |
| 35 | — | 0 | — | — |
| 36 | — | 4 | — | — |
| 37 | — | 29 | — | — |
| 38 | — | 100 | — | — |
| 40 | — | 0 | — | — |
| 44 | — | 46 | — | — |
| 47 | — | 54 | — | — |

[1]Average of 3-4 replicates. Untreated check showed no control.
[2]Percent control is $$\frac{\left(\frac{\text{Nematode Count in Check}}{\text{Root Weight in Check}}\right) - \left(\frac{\text{Nematode Count in Treatment}}{\text{Root Weight in Treatment}}\right)}{\left(\frac{\text{Nematode Count in Check}}{\text{Root Weight in Check}}\right)} \times 100$$

We claim:

1. A method for the control of nematodes by applying to the soil at the situs of infestation a nematicidally effective amount of a nematicidal composition containing as active ingredient a compound of the formula:

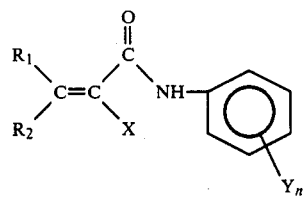

wherein $R_1$ and $R_2$ are indendently hydrogen, lower alkyl, or halogen;

X is hydrogen or halogen, with the proviso that at least one of $R_1$, $R_2$ and X must be halogen;

n is 1 or 2;

Y is hydrogen, lower alkyl, halogen, trifluoromethyl, lower alkoxy, lower alkylthio, and nitro when n is 1, and halogen when n is 2.

2. The method of claim 1 in which $R_1$ and $R_2$ are hydrogen and X is chlorine or bromine.

3. The method of claim 2 in which n is 1 and Y is hydrogen, 4-chloro, 4-methyl, or 4-methoxy.

4. The method of claim 1 in which $R_1$ is hydrogen, $R_2$ is methyl, and X is bromine.

5. The method of claim 4 in which n is 1 and Y is 4-chloro, 4-bromo, 2-fluoro, 3-fluoro, 4-fluoro, 4-methyl, 4-methoxy, 4-methylthio, or 4-nitro.

* * * * *